US011542607B2

(12) United States Patent
Ou et al.

(10) Patent No.: US 11,542,607 B2
(45) Date of Patent: *Jan. 3, 2023

(54) PROCESS FOR THE RAPID BLACKENING OF SURGICAL NEEDLES

(71) Applicant: Ethicon, Inc., Somerville, NJ (US)

(72) Inventors: Duan Li Ou, Warren, NJ (US); Christophe Vailhe, Hillsborough, NJ (US); Inas Alhamyery, Rellingen (DE)

(73) Assignee: Ethicon, Inc., Raritan, NJ (US)

( * ) Notice: Subject to any disclaimer, the term of this patent is extended or adjusted under 35 U.S.C. 154(b) by 584 days.

This patent is subject to a terminal disclaimer.

(21) Appl. No.: 16/437,542

(22) Filed: Jun. 11, 2019

(65) Prior Publication Data

US 2019/0301024 A1    Oct. 3, 2019

Related U.S. Application Data

(63) Continuation of application No. 15/190,437, filed on Jun. 23, 2016, now Pat. No. 10,364,501.

(51) Int. Cl.
*C23C 22/73* (2006.01)
*A61B 17/06* (2006.01)
(Continued)

(52) U.S. Cl.
CPC ........ *C23C 22/73* (2013.01); *A61B 17/06066* (2013.01); *A61B 17/3417* (2013.01);
(Continued)

(58) Field of Classification Search
None
See application file for complete search history.

(56) References Cited

U.S. PATENT DOCUMENTS

| 2,817,610 A | 12/1957 | Newell |
| 3,314,812 A | 4/1967 | Mitchell |

(Continued)

FOREIGN PATENT DOCUMENTS

| CN | 1050572 A | 4/1991 |
| CN | 101935833 A | 1/2011 |

(Continued)

OTHER PUBLICATIONS

Practice Tutorials of Metallic Material Engineering, edited by Li Xuewei, p. 144, Harbin Institute of Technology Press, Mar. 2014.
(Continued)

*Primary Examiner* — Lois L Zheng
(74) *Attorney, Agent, or Firm* — Amir Bishara (57) ABSTRACT

A novel method of blackening surgical needles is disclosed. Surgical needles having outer surfaces are first placed into a first pretreatment bath having a novel composition. The needles are then placed into a second blackening bath having a novel composition for a sufficient period of time to effectively blacken the surfaces of the needles. The novel methods for blackening the surfaces of a stainless steel alloy surgical needle provide a chromium (VI)-free alternative to current needle manufacturing processes. Another unique feature of this novel method is its short processing time. The blackening processes of the present invention can be utilized for in-line treatment processes which can be easily incorporated into high speed needle manufacturing processes, such as strip mounted processes. In addition, the processes of the present invention are readily adaptable to batch processes. Also disclosed are novel systems for blackening surgical needles and novel blackening baths for surgical needles.

24 Claims, 4 Drawing Sheets
(2 of 4 Drawing Sheet(s) Filed in Color)

(51) Int. Cl.
    *C23C 22/50*     (2006.01)
    *C23C 22/62*     (2006.01)
    *C23G 1/08*     (2006.01)
    *A61B 17/34*     (2006.01)
    *C23C 22/68*     (2006.01)
    *C23C 22/78*     (2006.01)
    *C23C 22/06*     (2006.01)
    *A61L 17/14*     (2006.01)
    *A61B 17/00*     (2006.01)

(52) U.S. Cl.
    CPC .............. *C23C 22/50* (2013.01); *C23C 22/62* (2013.01); *C23C 22/68* (2013.01); *C23C 22/78* (2013.01); *C23G 1/08* (2013.01); *C23G 1/081* (2013.01); *C23G 1/083* (2013.01); *C23G 1/085* (2013.01); *A61B 2017/00526* (2013.01); *A61B 2017/00831* (2013.01)

(56) References Cited

U.S. PATENT DOCUMENTS

| | | |
|---|---|---|
| 5,000,912 A | 3/1991 | Bendel et al. |
| 5,104,463 A | 4/1992 | Menke |
| 5,181,416 A | 1/1993 | Evans |
| 5,718,745 A | 2/1998 | Itoh |
| 7,887,746 B2 | 2/2011 | Cichocki et al. |

FOREIGN PATENT DOCUMENTS

| | | | |
|---|---|---|---|
| CN | 102965652 A | 3/2013 | |
| CN | 104233275 A | 12/2014 | |
| CN | 104357826 A | 2/2015 | |
| EP | 0405340 A1 | 1/1991 | |
| EP | 0168833 B2 | 10/1994 | |
| EP | 1051538 B1 | 10/2003 | |
| JP | 57101658 A | 6/1982 | |
| JP | 60-190588 * | 9/1985 | ............... C25D 3/12 |
| JP | 61045745 A | 3/1986 | |
| JP | H01195286 A | 7/1989 | |
| JP | 9316657 A | 12/1997 | |
| JP | H09316657 A | 12/1997 | |
| JP | 2001158982 A | 6/2001 | |
| JP | 2006028573 A | 2/2006 | |
| JP | 2011509144 A | 3/2011 | |
| WO | 99/39024 A1 | 8/1999 | |

OTHER PUBLICATIONS

China Search Report 201780038814.6 dated Aug. 12, 2020.
European Examination Report 17734196.3 dated Jun. 17, 2021.
Japan Preliminary Report 2018-567211 dated Mar. 22, 2021.
Anoshchenko I L et al: "Pickling of Steel in Phosphoric Acid With the Addition of Sodium Chloride and Alpha-Pyrrolidone Tar", Protection of Metals, vol. 26, No. 3, May 1990 (May 1990), pp. 398-399, XP000228109, Plenum Publishing Co., NY [US] ISSN: 0033-1732.

\* cited by examiner

FIG. 5. Auger Surface Analysis of Example 6.

PROCESS FOR THE RAPID BLACKENING OF SURGICAL NEEDLES

This application is a continuation of and claims priority to U.S. patent application Ser. No. 15/190,437 filed Jun. 23, 2016. The complete disclosures of the aforementioned related U.S. patent application is hereby incorporated herein by reference for all purposes.

FIELD OF THE INVENTION

The field of art to which this invention pertains is manufacturing processes for surgical needles, more particularly, processes for blackening the surfaces of surgical needles.

BACKGROUND OF THE INVENTION

Surgical needles are typically made from conventional metals such as surgical stainless steels and other biocompatible metal alloys. The needles desirably have smooth outer surfaces to facilitate the passage through tissue and minimize the adherence of contaminants or foreign substances. The needle surfaces are typically polished to provide smooth surfaces that are bright, shiny and reflective. Surgical needles are typically coated with silicone coatings to improve the penetration of the needles through multiple passes in tissue.

In certain types of surgical procedures such as endoscopic and laparoscopic surgical procedures, the surgeon views the site of the procedure remotely via a camera and a screen display of the surgical field. It is known that in such procedures the surgical team may have difficulty in seeing a conventional surgical needle because of the shiny reflective surfaces. This is particularly true of the distal end of the needle having the tissue piercing point. The inability to quickly and efficiently locate the needle and needle tip when conducting a laparoscopic suturing procedure has led to the development of surgical needles having blackened surfaces. The blackened needles have proven to have better visibility in the surgical field and are often preferred in minimally invasive surgical procedures utilizing indirect visualization.

Blackening processes for blackening the bright, shiny surfaces of surgical needles are known in this art. The processes may include chemical baths, exposure to plasmas, laser energy, oxidizing fumes, etc. The objective of the blackening processes is to form an iron oxide ($Fe_2O_4$)-based layer on the surfaces of the stainless steel needles which provides the blackened appearance.

The chemical baths used in the prior art processes typically contain Chromium (VI) as a component of the baths. Such processes are often lengthy and typically require process times in excess of twenty hours to provide effectively blackened surfaces on the needles.

Although the chemical needle blackening processes of the prior art are effective in providing blackened surfaces on surgical needles, there are known deficiencies associated with their use. First of all, the use of blackening baths containing the requisite high concentrations of Chromium (VI) compounds presents both environmental risks and safety hazards. The safety hazards include the carcinogenicity of the Chromium (VI) compounds. Chronic inhalation of hexavalent chromium compounds is known to increase the risk of lung cancer. (The lungs are the most vulnerable, followed by the fine capillaries in kidneys and intestines). Soluble Chromium (VI) compounds in conventional needle blackening solutions can cause or exacerbate contact dermatitis. Ingestion of chromium VI can also cause irritation or ulcers in the stomach and intestines. The environmental risks associated with Chromium (VI)-containing blackening baths include ground water and soil contamination, which leads to the risk of exposure to humans, domestic and farm animals, and wildlife. In addition to the safety hazards and environmental risks associated with such processes, it is known that the existing processes are extremely slow, typically requiring process times in excess of 20 hours up to 36 hours in order to achieve sufficiently effective blackening. This necessitates that such blackening processes are batch-type processes in which larger batches of needles are immersed in the blackening baths. The conventional processes cannot be used with high speed needle manufacturing processes wherein needles are mounted to strips and moved at a relatively high rate of speed to and from various manufacturing steps. Finally, the existing processes are not cost effective for a variety of reasons including production efficiency, generation and disposal of hazardous waste, burdensome engineering controls, substantial safety requirements, potential liability, etc.

Accordingly, there is a need in this art for novel methods and processes for blackening surgical needles that eliminate the need for Chromium (VI) compounds in blackening baths. There is a further need for blackening methods and processes that provide quick process times, are environmentally friendly, safe to operate, and are cost effective.

SUMMARY OF THE INVENTION

Therefore a novel method of blackening the surfaces of surgical needles is disclosed. In the novel method of the present invention, at least one surgical needle having an outer surface is placed into a pretreatment bath. The pretreatment bath contains about 8 wt. % to about 20 wt. % of a water soluble chloride salt, about 5 wt. % to about 15 wt. % of an inorganic acid, and about 60 wt. % to about 90 wt. % of water. The pretreatment bath has a pH of about 0.5 to about 1.2. The surgical needle is then placed into a blackening bath. The blackening bath contains about 3 wt. % to about 20 wt. % of a highly soluble nitric acid salt, about 18 wt. % to about 38 wt. % of a strong base, about 50 wt. % to about 75 wt. % of water, about 0.2 wt. % to about 5 wt. % of a transition metal salt of a strong acid, and about 0.2 wt. % to about 5 wt. % of a sulfur-containing reducer compound. The needle is maintained in the bath for a sufficiently effective period of time to provide a blackened coating on the outer surfaces of the needle.

Another aspect of the present invention is a novel method of blackening the surfaces of surgical needles. In the novel method of the present invention, at least one surgical needle having an outer surface is placed into a pretreatment bath. The pretreatment bath contains about 8 wt. % to about 20 wt. % of a water soluble chloride salt, about 5 wt. % to about 15 wt. % of an inorganic acid, and about 60 wt. % to about 90 wt. % of water. The pretreatment bath has a pH of about 0.5 to about 1.2. The surgical needle is then placed into a blackening bath. The blackening bath contains about 3 wt. % to about 20 wt. % of a highly soluble nitric acid salt, about 18 wt. % to about 38 wt. % of a strong base, about 50 wt. % to about 75 wt. % of water, about 0.2 wt. % to about 5 wt. % of a highly soluble permanganate salt, and about 0.2 wt. % to about 5 wt. % of a thiocyanate salt. The needle is maintained in the bath for a sufficiently effective period of time to provide a blackened coating on the outer surfaces of the needle.

Yet another aspect of the present invention is a novel composition for use as a needle blackening bath. The composition contains about 3 wt. % to about 20 wt. % of a highly soluble nitric acid salt, about 18 wt. % to about 38 wt. % of a strong base, about 50 wt. % to about 75 wt. % of water, about 0.2 wt. % to about 5 wt. % of a transition metal salt of a strong acid, and about 0.2 wt. % to about 5 wt. % of a sulfur-containing reducer compound.

Still yet another aspect of the present invention is a novel composition for use as a needle blackening bath. The composition contains about 3 wt. % to about 20 wt. % of a highly soluble nitric acid salt, about 18 wt. % to about 38 wt. % of a strong base, about 50 wt. % to about 75 wt. % of water, about 0.2 wt. % to about 5 wt. % of a highly soluble permanganate salt, and about 0.2 wt. % to about 5 wt. % of a thiocyanate salt.

An additional aspect of the present invention is a system for blackening stainless steel alloy surgical needles. The system has a pretreatment bath and a blackening bath. The pretreatment bath contains about 8 wt. % to about 20 wt. % of a water soluble chloride salt, about 5 wt. % to about 15 wt. % of an inorganic acid, and about 60 wt. % to about 90 wt. % of water. The pretreatment bath has a pH of about 0.5 to about 1.2. The blackening bath contains about 3 wt. % to about 15 wt. % of a highly soluble nitric acid salt, about 18 wt. % to about 38 wt. % of a strong base, about 50 wt. % to about 75 wt. % of water, about 0.2 wt. % to about 5 wt. % of a transition metal salt of a strong acid, and about 0.2 wt. % to about 5 wt. % of a sulfur-containing reducer compound.

A further aspect of the present invention is a system for blackening stainless steel alloy surgical needles. The system has a pretreatment bath and a blackening bath. The pretreatment bath contains about 8 wt. % to about 20 wt. % of a water soluble chloride salt, about 5 wt. % to about 15 wt. % of an inorganic acid, and about 60 wt. % to about 90 wt. % of water. The pretreatment bath has a pH of about 0.5 to about 1.2. The blackening bath contains about 3 wt. % to about 20 wt. % of a highly soluble nitric acid salt, about 18 wt. % to about 38 wt. % of a strong base, about 50 wt. % to about 75 wt. % of water, about 0.2 wt. % to about 5 wt. % of a highly soluble permanganate salt, and about 0.2 wt. % to about 5 wt. % of a thiocyanate salt.

These and other aspects and advantages of the present invention will become more apparent from the following description and accompanying drawings.

BRIEF DESCRIPTION OF THE DRAWINGS

The patent or application file contains at least one drawing executed in color. Copies of this patent with color drawing(s) will be provided by the Patent and Trademark Office upon request and payment of necessary fee.

DETAILED DESCRIPTION OF THE INVENTION

The surgical needles that can be blackened using the novel process of the present invention will include conventional surgical needles having conventional shapes made from conventional surgical grade stainless steel alloys. The stainless steel alloys will include but not be limited to Type 455, Type 316, Type 4310, Type 420, and the like. Another type of stainless steel alloy that can be blackened using the processes of the present invention is the proprietary alloy "ETHALLOY" available from Ethicon, Inc., Somerville, N.J. 08876 USA. The composition of ETHALLOY alloy is described in U.S. Pat. No. 5,000,912, which is incorporated by reference. The processes, baths and systems of the present invention can also be used to blacken the surfaces of other types of medical devices, in addition to needles, made from such alloys.

The processing equipment useful in the practice of the present invention will include conventional processing equipment such open vats, tanks, mixing apparatus, and baskets. The equipment may include specially designed and adapted tanks for receiving needles on strips when using high speed needle manufacturing processes. The equipment will be made of conventional corrosion resistant materials such as Nylon, glass, PEEK, Teflon, PVDF, and the like. The equipment may be made of conventional metals such as aluminum, and stainless steel that have had their contact surfaces coated with conventional corrosion resistant coatings such as ceramic, PTFE, FEP, and the like.

The baths used in the pretreatment step of the process of the present invention will be aqueous-based compositions. The pretreatment baths will have sufficient quantities of the bath ingredients to provide for effective pretreatment. The pretreatment baths will typically contain about 8 wt. % to about 20 wt. % of a water soluble chloride salt, more typically about 10 wt. % to about 18 wt. %, and preferably about 15 wt. % to about 17 wt. %. The pretreatment baths will also contain about 5 wt. % to about 15 wt. % of an inorganic acid, more typically about 6 wt. % to about 10 wt. %, and preferably about 7 wt. % to about 8 wt. %. And, the pretreatment baths will typically contain about 60 wt. % to about 90 wt. % of water, more typically about 70 wt. % to about 80 wt. %, and preferably about 75 wt. % to about 78 wt. %. The water soluble chloride salts useful in the pretreatment baths include but are not limited to sodium chloride, potassium chloride, lithium chloride and the like. The inorganic acids useful in the pretreatment baths include but are not limited to phosphoric acid, sulfuric acid, hydrochloric acid, nitric acid, and the like. The pH of the pretreatment baths will typically range from about 0.1 to about 1.2, more typically about 0.3 to about 1, and preferably about 0.5 to about 0.8.

The blackening bath compositions useful in the blackening processes of the present invention will be aqueous-based compositions. The blackening baths will have sufficient quantities of the bath ingredients to provide for effective blackening of the surfaces of needles. The blackening baths will typically contain about 18 wt. % to about 38 wt. % of a strong base, more typically about 20 wt. % to about 35 wt.

%, and preferably about 26 wt. % to about 30 wt. %. The blackening baths of the present invention will typically contain about 3 wt. % to about 20 wt. % of a highly soluble nitric acid salt, more typically about 5 wt. % to about 15 wt. %, and preferably about 11 wt. % to about 13 wt. %. And the blackening baths will typically contain about 50 wt. % to about 75 wt. % of water, more typically about 55 wt. % to about 70 wt. %, and preferably about 58 wt. % to about 65 wt. %. The nitric acid salts useful in the blackening baths of the present invention include but are not limited to sodium nitrate, potassium nitrate, lithium nitrate, and the like. The strong bases useful in the blackening baths of the present invention include but are not limited to sodium hydroxide, potassium hydroxide, lithium hydroxide, and the like.

In a first embodiment, the blackening baths of the present invention will also contain components containing two different precursors to form transition metal sulfides. The first precursor is a transition metal salt of a strong acid. Such precursors include but are not limited to nickel nitrate, cobalt nitrate, nickel sulphate, cobalt sulphate, iron nitrate, copper perchlorate, nickel perchlorate, ion perchlorate, and cobalt perchlorate and the like. The second precursor is a sulfur-containing reducer. Such second precursors include but are not limited to N,N'-diethylthiourea, sodium thiocyanate, sodium sulfide, and sodium dimethyldithiocarbamate and the like. The transition metal sulfide compounds that are formed may include, but are not limited to, NiS, CoS, $Ag_2S$, etc. The amount of the transition metal salt of a strong acid included in this embodiment of the blackening baths of the present invention is typically about 0.1 wt. % to about 3 wt. %, more typically about 0.2 wt. % to about 2 wt. %, and preferably about 0.3 wt. % to about 1 wt. %. The amount of the sulfur-containing reducer included in this embodiment of the blackening baths of the present invention is typically about 0.1 wt. % to about 3 wt. %, more typically about 0.2 wt. % to about 2 wt. %, and preferably about 0.3 wt. % to about 1 wt. %.

In a second embodiment, the blackening baths of the present invention will also contain manganese-containing oxidizers, also referred to as highly soluble permanganate salts, including but not limited to potassium permanganate, sodium permanganate, and lithium permanganate, and the like. The baths in the second embodiment will also contain a thiocyanate salt. The thiocyanate salts useful in this embodiment of the blackening baths include but are not limited to as sodium thiocyanate, potassium thiocyanate, lithium thiocyanate, and the like. The amount of the manganese-containing oxidizer (highly soluble permanganate salt) in this second embodiment of the blackening baths of the present invention is typically about 0.1 wt. % to about 5 wt. %, more typically about 0.2 wt. % to about 3 wt. %, and preferably about 0.3 wt. % to about 1 wt. %. The amount of the thiocyanate salt included in this embodiment of the blackening baths of the present invention is typically about 0.1 wt. % to about 5 wt. %, more typically about 0.2 wt. % to about 3 wt. %, and preferably about 0.3 wt. % to about 1 wt. %.

The second embodiment of the blackening baths may optionally include several additives to enhance the color of the black oxide layer, and enable the repeat usage of the blackening bath. The additives include and are not limited to 1. molybdate salts including ammonium molybdate, sodium molybdate and potassium molybdate; and, 2. sodium chloride. The amount of molybdate salts optionally present in this embodiment will be sufficient to provide effective blackening enhancement and would typically range from 0.1 wt. % to about 3 wt. %. The amount of sodium chloride optionally present in this embodiment will be sufficient to provide effective blackening enhancement and would typically range from 0.3 wt. % to about 1 wt. %.

The pretreatment bath compositions and the blackening bath compositions may be made in a conventional manner using conventional process and mixing equipment. For example, the blackening and pretreatment bath compositions may be made in the following manner: mixing all of the components using a mechanical mixer for a sufficiently effective time up to about one hour until all of the solid components are fully dissolved in the aqueous solution.

The novel methods of the present invention for blackening surgical needles consist of two primary steps. The initial step is a pretreatment step that is performed prior to the needle blackening step. In the pretreatment step surface oxides are removed from the surfaces of the needles. The second step is the needle blackening step. In the blackening step, a black oxide coating is formed on the surfaces of the needles.

The pretreatment step is directed toward the removal of surface oxides. Stainless steels are covered with a layer of chromium oxide which makes them corrosion resistant. This oxide layer results in the surface being passivated and resists further chemical treatment. The activating solution reacts with chromium oxide and enables the surfaces of the stainless steel needles to be chemically receptive to the various blackening solutions utilized in the second blackening step. Any surface contaminants present on the needles surfaces such as machine oil and grease will also be removed during this step. Various acids such as hydrochloric acid, phosphoric acid and sulfuric acid are commonly used at elevated temperature for this purpose. Therefore, the first step is also referred to as a pickling process step which typically lasts about 10 minutes to about one hour. The formulation for a pretreatment bath listed below in Table 1 was developed for a 30 second activation process adapted to an in-line process and 3 minutes for a large scale batch process. The process temperature for this bath formulation is 80° C., well below the boiling point of the solution to prevent fume formation of hazardous material.

In the pretreatment process, a pretreatment bath solution as described above and in the Tables and Examples is prepared using conventional mixing equipment and process equipment. The solution is transferred to a conventional bath vessel having the desired dimensions and volumetric capacity. The pretreatment process step can be conducted as a batch process or a continuous process. It will be appreciated that the bath configuration will also depend on whether the pretreatment process is batch or continuous. In a batch process, the needles are typically loaded into a basket and immersed in the bath in the bath solution. The needles are maintained in the bath for a sufficient period of time at a sufficient temperature to effectively pretreat the surfaces of the needles. The time will typically range from about 30 seconds to about 1 hour, more typically about 1 minute to about 30 minutes, and preferably about 2 minutes to about 5 minutes, depending upon on the amount of needles in the batch. The temperature of the pretreatment bath will typically range from about 60° C. to about 100° C., more typically about 70° C. to about 90° C., and preferably about 75° C. to about 85° C.

In a continuous process, needles are typically mounted to a strip for rapid movement between manufacturing stations in a high speed needle operation. In such a process, the strip mounted needles are moved through the pretreatment bath while mounted to the strip. The needles are maintained in the bath for a sufficient period of time at a sufficient temperature to effectively pretreat the surfaces of the needles. The time will typically range from about 20 seconds to about 60 seconds, more typically about 25 seconds to about 45 seconds, and preferably about 30 seconds to about 40 seconds. The temperature of the pretreatment bath will typically range from about 60° C. to about 100° C., more typically about 70° C. to about 80° C., and preferably about 75° C. to about 85° C.

The blackening process is performed in a similar manner to the pretreatment process. In the blackening process, a blackening bath solution as described above is prepared using conventional mixing equipment and process equipment. The solution is transferred to a conventional bath vessel having the desired dimensions and volumetric capacity. The blackening process step can be conducted as a batch process or a continuous process. It will be appreciated that the bath configuration will also depend on whether the blackening process is batch or continuous. In either case, the bath may be optionally agitated by conventional equipment. In a batch process, the needles are typically loaded into a basket and immersed in the bath in the bath solution. The quantity of needles in a batch will vary with the size of the system, and may range for example from less than 10 to more than 10,000 needles. The needles are maintained in the bath for a sufficient period of time at a sufficient temperature to effectively treat the surfaces of the needles to obtain blackened surfaces. The time will typically range from about 1 minute to about 60 minutes, more typically about 2 minutes to about 30 minutes, and preferably about 2 minutes to about 4 minutes. The temperature of the blackening treatment bath will typically range from about 90° C. to about 140° C., more typically about 95° C. to about 110° C., and preferably about 98° C. to about 105° C. In a continuous process, needles are typically mounted to a strip for rapid movement between manufacturing stations in a high speed needle operation. In such a process, the strip mounted needles are moved through the blackening bath while mounted to the strip. The needles are maintained in the bath for a sufficient period of time at a sufficient temperature to effectively blacken the surfaces of the needles. The typical number of needles in the treatment bath may range, for example, from 20 or less to 100 or more needles at one time. The treatment time will typically range from about 5 seconds to about 40 seconds more typically about 10 seconds to about 30 seconds, and preferably about 15 seconds to about 25 seconds. The temperature of the blackening treatment bath will typically range from about 90° C. to about 140° C., more typically about 95° C. to about 110° C., and preferably about 98° C. to about 105° C.

Unlike the acid/Cr(VI)-based processes currently used in this art, the novel processes of the present invention are alkali-based processes that provide for and enable the rapid formation of black oxide on the surface of stainless steel surgical needles. The activated stainless steel needles are immersed into an aqueous alkaline solution consisting of sodium hydroxide, sodium nitrate and several other minor components (the basic composition of the blackening solution is outlined in Table 2, the weight % of each minor component is typically less than 0.5) at an elevated temperature below its boiling point, which is different from other conventional and commercial blackening processes. This substantially reduces or eliminates toxic fume formation during the blackening process step. Using the novel process of the present inventions, it has been observed, surprisingly and unexpectedly, that small batches of needles (under 50 units) are blackened within 30 seconds (can be as short as 10 seconds), and large batches of needles (up to several thousand or more) are blackened after 2 minutes immersion in the novel blackening bath solutions of the present invention. The process temperature is 100° C., well below the boiling point of the solution to substantially reduce or eliminated the formation of fumes containing hazardous materials.

Similar to the prior art Cr(VI) based blackening process, in which the black oxide ($Fe_3O_4$) layer is formed alongside the formation of $Cr_2O_3$, the formation of a second ceramic material is needed to start to iron oxide formation in the novel blackening process of the present invention. The minor components in the formulation are the precursors for the second phase ceramic material. Typically two different types of minor components are used in the formulation:

Type 1 components containing two different precursors to form transition metal sulfide.

1. Transition metal salt of strong acid, such as nickel nitrate, cobalt nitrate, nickel sulfate, cobalt sulfate, iron nitrate, copper perchlorate, nickel perchlorate, ion perchlorate, cobalt or perchlorate; and, 2. Sulfur-containing reducer compounds, such as N,N'-diethylthiourea, sodium thiocyanate, sodium sulphide, sodium dimethyldithiocarbamate.

Transition metal sulfides will form on the surface of stainless steel as the result of the blackening process with Type 1 components.

Type 2 components containing manganese-containing oxidizers such as potassium permanganate, and several additives as previously described to enhance the color of the black oxide layer, and enable the repeated usage of the blackening baths.

Manganese oxides will form on the surface of stainless steel as a result of the blackening process with Type 2 components.

A stabilizer may also be used in the blackening bath formulations of the present invention to enable multiple usage and prolong the pot life of the blackening solution. An example of stabilizers for incorporation in the blackening bath solution includes and is not limit to sodium chloride, ammonium molybdate, sodium thiocyanate, and sodium cyanate. The blackening solution is capable of being used multiple times after the addition of a stabilizer compound. The color of the resulting blackened needles remains consistent between batches after repeat usage of the blackening solution. This provides the advantage of improved production capability and minimizes the amounts of chemical waste generated from the blackening process.

Figure 1:
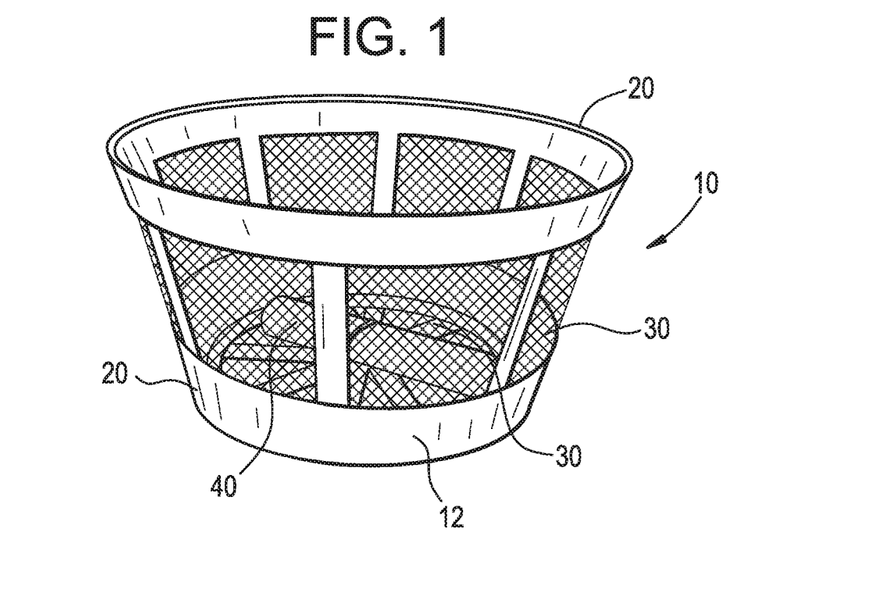
FIG. 1 is a photograph showing a side perspective view of a rotational basket useful in the practice of the present invention; a magnetic bar is mounted to the interior bottom of the basket.
Figure 2:
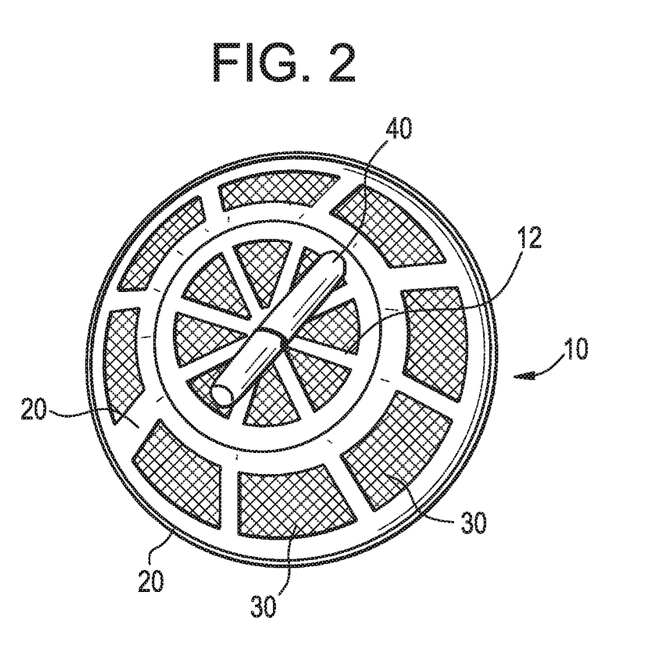
FIG. 2 is a photograph of a top perspective view of the basket of FIG. 1 showing a magnetic bar mounted to the bottom of the basket.

In the following examples, a novel rotational basket 10 was used for both steps of the needle blackening process. The structure of the basket is illustrated in FIGS. 1 and 2. High temperature plastic such as nylon or high density polypropylene (HDPP) was used to construct the frame 20 of the basket 10. Nylon mesh 30 was used to cover the entire frame 20 of basket 10 to allow the chemical solutions used in both steps to penetrate through and react with the surface of thousands of needles contained in a batch inside the basket. The rotating mechanism consists of a magnetic bar 40 mounted on the bottom 12 of the mesh basket 10 as seen in FIG. 1. The mesh basket 10 is able to rotate at a controllable speed on a conventional magnetic stirrer. This equipment allows a substantial amount of needles (e.g., over 3,000 larger needles and over 20,000 micro needles) to be blackened in a short period of time (e.g., 5 minutes). The full and complete exposure of the entire batch of surgical needles to the blackening solution allows all of the surfaces of each needle to be converted to a black color (homogeneous colorization). The gentle rotation provide by this basket prevents point damage that may occur and be caused by needle collisions during agitation.

The following examples are illustrative of the principles and practice of the present invention, although not limited thereto:

TABLE 1

Composition of Activating Solution.

| Material | Weight (%) |
| --- | --- |
| Sodium Chloride | 16.7 |
| Phosphoric Acid (85% in water) | 9.0 |
| Water | 74.3 |

TABLE 2

Composition of Blackening Solution.

| Material | Weight (%) |
| --- | --- |
| Sodium hydroxide | 28 |
| Sodium nitrate | 12 |
| Water | 60 |

Example 1

Formation of Nickel Sulfide-Containing Iron Oxide Black Layer

A small amount of transition metal salt (nickel nitrate) and sulfide precursor (sodium sulfide) was added to an alkaline solution of sodium nitrate as listed in Table 2 and the formulation of this blackening solution is listed in Table 3.

TABLE 3

Formulation of Blackening Solution

| Component | Formula | Weight (g) |
| --- | --- | --- |
| Sodium Nitrate | $NaNO_3$ | 15 |
| Sodium Hydroxide | NaOH | 35 |
| Water | $H_2O$ | 75 |
| Nickel(II) Nitrate Hexahydrate | $NiNO_3 \cdot 6H_2O$ | 1 |
| Sodium Sulfide Nonahydrate | $Na_2S \cdot 9H_2O$ | 3 |

A quantity of thirty (30) 22 mil type 4310 SH needles (manufactured by Ethicon, Inc.) was immersed in a bath containing the activating solution listed in Table 1 at 80° C. for 2 minutes. The needles were then rinsed with water and immersed into a bath containing the blackening solution listed in Table 3 at 100° C. for 1 minute. The surfaces of the silver needles turned completely black.

Example 2

Formation of Copper Sulfide-Containing Iron Oxide Black Layer

A small amount of transition metal salt (copper nitrate) and sulfide precursor (sodium sulfide) was added to an alkaline solution of sodium nitrate listed in Table 2 and the formulation of this blackening solution is summarized in Table 4.

TABLE 4

Formulation of Blackening Solution.

| Component | Formula | Weight (g) |
| --- | --- | --- |
| Sodium Nitrate | $NaNO_3$ | 15 |
| Sodium Hydroxide | NaOH | 35 |
| Water | $H_2O$ | 75 |
| Copper(II) Nitrate Trihydrate | $CuNO_3 \cdot 3H_2O$ | 1 |
| Sodium Sulfide Nonahydrate | $Na_2S \cdot 9H_2O$ | 3 |

A quantity of thirty (30) 22 mil type 4310 SH needles (manufactured by Ethicon, Inc.) was immersed in a bath containing the activating solution listed in Table 1 at 80° C. for 2 minutes. The needles were removed and rinsed with water, and then immersed in a bath containing the blackening solution listed in Table 4 at 100° C. for 1 minute. The color of the surfaces of the silver needles turned completely black.

Example 3

Formation of Cobalt Sulfide-Containing an Iron Oxide Black Layer

A small amount of transition metal salt (cobalt nitrate) and sulfide precursor (sodium sulfide) was added to an alkaline solution of sodium nitrate listed in Table 2. The formulation of this blackening solution is summarized in Table 5.

TABLE 5

Formulation of Blackening Solution

| Component | Formula | Weight (g) |
| --- | --- | --- |
| Sodium Nitrate | $NaNO_3$ | 15 |
| Sodium Hydroxide | NaOH | 35 |
| Water | $H_2O$ | 75 |
| Cobalt(II) Nitrate Hexahydrate | $CoNO_3 \cdot 6H_2O$ | 1 |
| Sodium Sulfide Nonahydrate | $Na_2S \cdot 9H_2O$ | 3 |

A quantity of thirty (30) 22 mil type 4310 SH needles (manufactured by Ethicon, Inc.) was immersed in a bath containing the activating solution listed in Table 1 at 80° C. for 2 minutes, and removed and rinsed with water. The needles were then immersed in a bath containing the blackening solution listed in Table 5 at 100° C. for 1 minute. The needles were removed from the bath and it was observed that the surfaces of the needles turned black.

Example 4

Formation of Manganese Oxide Containing an Iron Oxide Black Layer

A small amount of potassium permanganate and Sodium thiocyanate was added to an alkaline solution of sodium nitrate as listed in Table 2 to form a blackening solution. The formulation of this blackening solution is listed in Table 6

TABLE 6

Formulation of Example 5 Blackening Solution.

| Component | Formula | Weight (g) |
| --- | --- | --- |
| Sodium Nitrate | $NaNO_3$ | 15 |
| Sodium Hydroxide | NaOH | 35 |

TABLE 6-continued

Formulation of Example 5 Blackening Solution.

| Component | Formula | Weight (g) |
| --- | --- | --- |
| Water | H$_2$O | 75 |
| Potassium Permanganate | KMnO$_4$ | 0.25 |
| Sodium Thiocyanate | NaSCN | 0.25 |

A quantity of twenty (20) 22 mil type 4310 SH needles (manufactured by Ethicon, Inc.) was immersed in a bath containing the activating solution listed in Table 1 at 80° C. for 2 minutes, and then rinsed with water. The needles were then immersed in a bath containing the blackening solution listed in Table 6 at 100° C. for one (1) minute after which they were removed from the bath. The silver needles turned into blackened needles. It was observed that the surfaces of the silver needles were completely blackened.

A larger batch trial was also conducted using bath solution volumes 8 times the scale of activation and blackening solutions (1 kg) for a batch of 750 of 24 mil type 4310 MH needles (manufactured by Ethicon, Inc.) in a similar manner with slight variations in the treatment time for each of the steps. This large batch of needles was placed in the rotational basket (See FIGS. 1 and 2) and dipped in a bath containing the activating solution at 80° C. for 2 minutes, removed and rinsed with water, and then immersed in a bath containing the blackening solution at 100° C. for 2 minutes. The needles were removed from the bath and it was observed that the surfaces of all of the silver needles in the batch were completely blackened.

Example 5

Formation of Manganese Oxide-Containing Iron Oxide Black Layer on the Surface of Surgical Needles Made from 4310 Alloy: Repeat Usage of the Blackening Solution Example 5 is similar to Example 4, with the addition of 0.1 g sodium chloride to the blackening solution. This enabled a faster blackening reaction and along with repeat usage of the blackening solution. The formulation of this blackening solution is contained in Table 7

TABLE 7

Formulation of Example 6 Blackening Solution.

| Component | Formula | Weight (g) |
| --- | --- | --- |
| Sodium Nitrate | NaNO$_3$ | 15 |
| Sodium Hydroxide | NaOH | 35 |
| Water | H$_2$O | 75 |
| Potassium Permanganate | KMnO$_4$ | 0.25 |
| Sodium Thiocyanate | NaSCN | 0.25 |
| Sodium Chloride | NaCl | 0.1 |

A batch of fifty (50) 22 mil type 4310 SH needles (manufactured by Ethicon, Inc.) was immersed in a bath containing the activating solution listed in Table 1 at 80° C. for 30 seconds, then removed and rinsed with water. The needles were then immersed in a bath containing the blackening solution listed in Table 7 at 100° C. for 10 seconds. The needles were removed from the bath and it was observed that the surfaces of all of the silver needles in the batch were completely blackened.

A larger batch trial was also conducted using bath solution volumes 8 times the scale activation and blackening solutions (1 kg scale) for a batch of 750 24 mil type 4310 MH needles (manufactured by Ethicon, Inc.) in a similar manner with a slight variation of treatment times for each of the steps. This large batch of needles was placed in the rotational basket (FIGS. 1 and 2) and dipped in the bath containing the activating solution at 80° C. for 2 minutes, removed and rinsed with water, and then immersed in a bath containing the blackening solution at 100° C. for 2 minutes. The needles were removed from the bath and it was observed that the surfaces of all of the silver needles in the batch were completely blackened.

The capability of the blackening solution to be used for additional blackening cycles was also investigated and tested. It was observed that by adding additional amounts of sodium thiocyanate and potassium permanganate as needed to maintain the blackening solution to the formulation of Table 7, the blackening solution could be repeatedly re-used to effectively blacken batches of 750 24 mil MH needles, using the same activation and blackening parameters. It was observed that the blackening solution in the bath could be reused for at least 10 times with the blackened color of the surfaces of the needles remaining consistent after each usage of the blackening solution.

Figure 5:
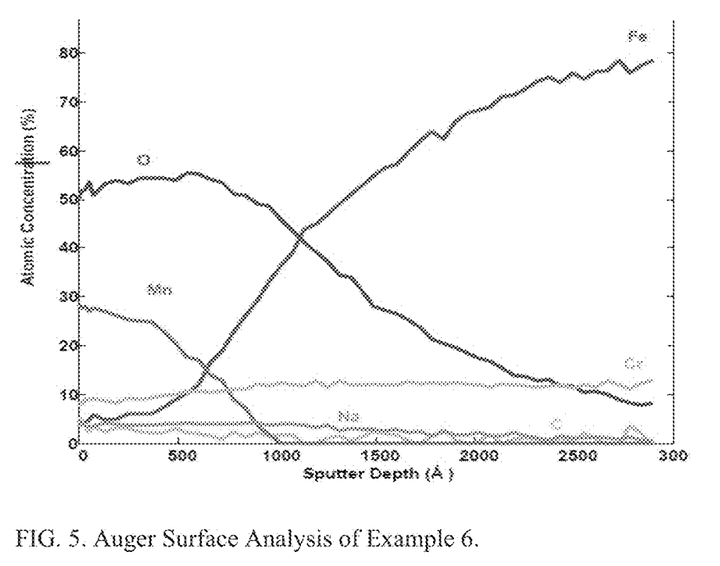
FIG. 5 is a graph showing Auger surface analysis of Example 5.

The MH needles of Example 5 were submitted for Auger Electron Spectroscopy analysis (Instrument model: PHI 680 Scanning Auger Microprobe), in order to measure the composition and thickness of the surface coating on this needle. A sputter depth profile revealed an oxide layer thickness of ~1,500 Å, as illustrated in FIG. 5. Manganese was the primary oxide in the outer ~750 Å of the surface and then a gradual increase in iron concentration was observed.

Example 6

Formation of Silicone Coated Needles Made from the Large Batch Production Described in Example 5

The entire batch of blackened 22 mil SH and 24 mil type 4310 MH needles from Example 5 was immersed in a silicone solution consisting of 50 g of Nusil MED 4162 and 450 g of heptane, prior to placing them on conventional craft paper and dried in a fume hood at ambient condition for 30 minutes. The silicone coated blackened needles were then cured in a conventional oven at 160° C. for one hour. A batch of regular (the silver needle) 22 mil type 4310 SH and 24 mil MH needles were also prepared in the same manor and used as control samples for the testing.

Coating performance for medical devices coated with silicone coating compositions can be tested with a variety of conventional friction or adhesion tests. In the case of surgical needles, coating performance, durability and integrity are evaluated using a conventional needle penetration testing device. A coated surgical needle is held using self-locking tweezers or a similar holding device. The coated needle is then passed through a polymeric medium that is selected to be representative of general human tissue. Approximately half of the needle length is passed through the medium and then retracted prior to the next pass. The test media may be a type of synthetic rubber (e.g., Duraflex™, Manufacture by Monmouth Rubber and Plastic Corporation, Monmouth, N.J.). A typical test includes using multiple needles that are individually passed through the media 20 times each. The maximum force is recorded for each pass and used as a measure of the coating performance. Typically the penetration force increases with each successive pass as the coating wears off from the needle. Further detail of the equipment and method can also be found in U.S. Pat. No. 5,181,416, which is incorporated by reference. ASTM F3014 is one example for a curved needle penetration test protocol.

Penetration testing was performed on these two sets of curved needles. The results obtained were from penetration testing done using samples of 30 individual needles. The average penetration force for each pass is summarized in Tables 8 and 9. The control samples for both sets of needles were also tested for the purpose of comparison, and the results are also included in these two tables.

TABLE 8

Needle Penetration Test: Example 6, 22 mil 4310 SH

|  | Avg. Force (g) 1$^{st}$ Pass | Stdv 1$^{st}$ Pass | Avg. Force(g) 10$^{th}$ Pass | Stdv 10$^{th}$ Pass | Avg. Force(g) 20$^{th}$ Pass | Stdv 20th Pass |
|---|---|---|---|---|---|---|
| Example 6 | 123 | 14.2 | 151 | 12.2 | 174 | 13.8 |
| Control (4310 SH needles) | 104 | 13.9 | 149 | 10.1 | 168 | 12.5 |

TABLE 9

Needle Penetration Test: Example 6, 24 mil 4310 MH

|  | Avg. Force (g) 1$^{st}$ Pass | Stdv 1$^{st}$ Pass | Avg. Force(g) 10$^{th}$ Pass | Stdv 10$^{th}$ Pass | Avg. Force(g) 20$^{th}$ Pass | Stdv 20th Pass |
|---|---|---|---|---|---|---|
| Example 6 | 121 | 14.1 | 180 | 14.0 | 231 | 16.1 |
| Control (4310 MH needles) | 108 | 12.7 | 180 | 11.2 | 218 | 12.0 |

Minor differences were found in the needle penetration results between both codes of 4310 blackened needles of Example 6 and the control samples. Such differences are within the error of measurement method (10% approx.). The blackening process illustrated in Example 6 did not create a negative impact on the penetration performance of the resulting blackened, curved needles.

Bending stiffness of the coated 22 mil type 4310 blackened SH needles was assessed according to ASTM F1874 on a set of 10 needles, against the control sample coated 22 mil regular shiny silver 4310 SH needles, and the results are summarized in Table 10.

As expected, the surface treatment to change the color of the needles did not have any significant impact on the stiffness and surgical yield of the needles. There was also no significant difference in the reshape values indicating that the blackening process had no effect on the bulk property of the alloy and did not sensitize the surface to crack formation. Most importantly, the blackened needles did not have a different "feel" or behavior to the user.

TABLE 10

Ethicon Bend Test Results (Average Values for 10 Needles).

|  | Current silver 22 mil SH needles | Blackened 22 mil SH needles from Example 6 |
|---|---|---|
| Reshape (number of bends before failure) | 2.6 (stdv = 0.4) | 2.9 (stdv = 0.2) |
| YM (gf * cm) (Surgical Yield) | 305.4 (stdv = 24.3) | 310.4 (stdv = 17.4) |
| Stiffness (Elastic Modulus) | 20.2 (stdv = 0.4) | 20.0 (stdv = 0.4) |

Example 7

Formation of Manganese Oxide-Containing Iron Oxide Black Layer on the Surface of Surgical Needles Made from Type 420 SS Alloy The blackening solution used in Example 5 (Table 8) was used for the sample preparation. A quantity of twenty (20) 24 mil 420 SH needles (manufactured by Ethicon, Inc.) was immersed in a bath containing the activating solution listed in Table 1 at 80° C. for 30 seconds. The needles were then rinsed with water and immersed in a bath containing the blackening solution listed in Table 7 at 100° C. for 30 seconds. The needles were removed from the bath and it was observed that the surfaces of all of the silver needles in the batch were completely blackened.

Example 8

Formation of Manganese-Oxide Containing Iron Oxide Black Layer on the Surface of Surgical Needles Made from ETHALLOY Alloy The blackening solution used in Example 5 (Table 7) was used for the sample preparation in this Example 8A and 8B.
8A—Loose ETHALLOY Needles for Batch Coating Trial with Nusil MED 4162 Silicone:

A quantity or batch of thirty (30) 24 mil ETHALLOY SH needles (manufactured by Ethicon, Inc.), cut out from a manufacturing process strip into loose needles was immersed in a bath containing the activating solution of Table 1 at 80° C. for 30 seconds, then removed and rinsed with water, and then immersed in a bath containing the blackening solution outlined in Table 7 at 100° C. for 30 seconds. The needles were removed from the bath and it was observed that the surfaces of all of the silver needles in the batch were blackened
8B—Strip with Mounted ETHALLOY Needles for Strip Coating Trial with Gelest XG-2385 Silicone:

A strip having a quantity of ten (10) 24 mil ETHALLOY SH needles (manufactured by Ethicon, Inc.) mounted thereto was immersed in a bath containing the activating solution outlined in Table 1 at 80° C. for 30 seconds, then rinsed with water, and then immersed in a bath containing the blackening solution of Table 7 at 100° C. for 30 seconds. The needles were removed from the bath and it was observed that the surfaces of all of the silver needles in the batch were completely blackened.
8C—Large Batch of Loose ETHALLOY Needles for Batch Coating Trial, Multiple Usage Cycles of Blackening Bath In order to address the color uniformity of ETHALLOY needles and the repeat usage of the blackening solution through successive cycles, an additional component, ammonium molybdate tetrahydrate was added into the base formulation of Table 7. The amount of the other additive, sodium chloride, was also increased. The formulation of this blackening solution is contained in Table 11.

TABLE 11

Formulation of Example 9C Blackening Solution.

| Component | Formula | Weight (g) |
|---|---|---|
| Sodium Nitrate | NaNO$_3$ | 120 |
| Sodium Hydroxide | NaOH | 280 |
| Water | 4H$_2$O | 600 |

TABLE 11-continued

Formulation of Example 9C Blackening Solution.

| Component | Formula | Weight (g) |
|---|---|---|
| Potassium Permanganate | $KMnO_4$ | 3 |
| Sodium Thiocyanate | NaSCN | 3 |
| Sodium Chloride | NaCl | 3 |
| Ammonium Molybdate tetrahydrate | $(NH_4)_6Mo_7O_{24} \cdot 4H_2O$ | 3 |

A batch of eight hundred sixty (860) 26 mil V-7 needles (manufactured by Ethicon, Inc.) was immersed in a bath containing the activating solution listed in Table 1 at 80° C. for 3 minutes, then removed and rinsed with water. The needles were then immersed in a bath containing the blackening solution listed in Table 11 at 100° C. for 1 hour. The needles were removed from the bath and it was observed that the surfaces of all of the silver needles in the batch were completely blackened.

The capability of the blackening solution to be used for additional blackening cycles was also investigated and tested. It was observed that by adding additional amounts of sodium thiocyanate and potassium permanganate as needed to maintain the blackening solution to conform to the formulation of Table 7, the blackening solution could be repeatedly re-used to effectively blacken batches of 860 26 mil V-7 needles, using the same activation and blackening parameters. It was observed that the blackening solution in the bath could be reused for at least 3 times with the blackened color of the surfaces of the needles remaining consistent after each usage of the blackening solution. It is believed that that blackening solution could be reused a significantly larger number of times by the addition of active components repeatedly as required to maintain the formulation.

Example 9

Batch Coat Needles of Example 8A

This example is directed to the formation of silicone coated Ethalloy SH needles made from the batch production highlighted in Example 8A, using a batch coating process similar to the one used in conventional Chromium-based blackened needle production. The entire batch of blackened 24 mil SH needles was immersed in a coating solution consisting of 50 g of Nusil MED 4162 and 450 g of heptane, prior to placing the needles on a craft paper substrate and then drying in a fume hood at ambient conditions for 30 minutes. The silicone coated blackened needles were then cured at 160° C. for one hour in a conventional convection oven.

Penetration testing was then performed, as described above, on a representative sample of the coated needles. The results are from penetration testing done using a sample of 10 individual needles. The coated needles were penetrated 20 times each. The average penetration force for each pass is summarized in Table 12.

TABLE 12

Needle Penetration Test: 24 mil Ethalloy SH, Batch Flow

| Needles | Avg. Force (g) $1^{st}$ Pass | Stdv $1^{st}$ Pass | Avg. Force(g) $10^{th}$ Pass | Stdv $10^{th}$ Pass | Avg. Force(g) $20^{th}$ Pass | Stdv $20^{th}$ Pass |
|---|---|---|---|---|---|---|
| Example 10 | 111 | 17.5 | 183 | 22.5 | 221 | 11.5 |

Example 10

Strip Coating Needles of Example 8B

This example is directed to the formation of silicone coated Ethalloy SH needles made from the strip process highlighted in Example 8B, using a strip coating process, in which all of the needles were mounted onto a metal strip and passed the coating solution in a dip tank in a continuous manner. The strip of blackened 24 mil SH needles was immersed in a bath containing a silicone coating solution consisting of 23.8 g of Gelest XG-2385A, 23.8 g Gelest XG-2385B and 52.4 g of Isopar K. The strip with the needles was removed from the bath and placed in a conventional oven at 195° C. for 30 seconds. The silicone coated blackened needles were further cured at 195° C. for 2 hours in a conventional convection oven.

Penetration testing was performed, as previously described, on the needles having cured silicone coatings. The results were from penetration testing done using a representative sample of 10 individual needles that were removed from the strip. The coated needles were penetrated 20 times each. The average penetration force for each pass listed in Table 13. The testing was conducted as described above.

TABLE 13

Needle Penetration Test: 24 mil Ethalloy SH, Strip Flow (Needle code 362409)

| Needles | Avg. Force (g) $1^{st}$ Pass | Stdv $1^{st}$ Pass | Avg. Force(g) $10^{th}$ Pass | Stdv $10^{th}$ Pass | Avg. Force(g) $20^{th}$ Pass | Stdv $20^{th}$ Pass |
|---|---|---|---|---|---|---|
| Example 11 | 57 | 2.3 | 82 | 14.7 | 95 | 19.5 |

A 57% reduction was observed on the $20^{th}$ pass penetration of the strip coated Ethalloy black SH needles (Example 10), compared to the same lot of needles coated with Nusil MED6162 using a batch process. The short reaction time enables the conversion of the needle blackening process to a strip flow and the usage of platinum cured silicone Gelest XG-2385 (Manufacture by Gelest, Inc., Morrisville, Pa.). Significant improvement on penetration performance can be achieved on blackened needles as demonstrated in this example.

Example 11

Comparative Example—Blackening Bath of Example 6 without NaNO3

This example is directed to the formation of dark green manganese containing iron oxide black layer on the surface of surgical needles made from Type 4310 SS alloy, instead of the black oxide layer demonstrated in Example 6. The formulation of this blackening solution is listed in Table 14.

TABLE 14

Formulation of Comparative Example 1 Solution.

| Component | Formula | Weight (g) |
|---|---|---|
| Sodium Hydroxide | NaOH | 280 |
| Water | $H_2O$ | 720 |
| Potassium Permanganate | $KMnO_4$ | 3 |
| Sodium thiocyanate | NaSCN | 3 |
| Sodium chloride | NaCl | 3 |

A quantity or batch of 750, 26 mil MH needles (manufactured by Ethicon, Inc.) was immersed in a bath containing the activating solution of Table 1 at 80° C. for 3 minutes, then rinsed with water, and then immersed in a bath containing the blackening solution listed in Table 14 at 100° C. for 2 minutes. After removal from the bath, the silver needles were observed to have a dark green appearance. Increasing the length of the process time in the bath solution did not change the color of the needles. It was not possible to obtain truly black needles as a result of treatment in the solution of this Table 14.

Example 12

Comparative Example—Blackening Bath of Example 6 without NaOH

This example did not lead to the formation of a black oxide black layer on the surfaces of surgical needles made from Type 4310 SS alloy in comparison to the black oxide layer demonstrated and obtained in Example 5. The formulation of the blackening bath solution used in this example is listed in Table 15.

TABLE 15

Formulation of Comparative Example 1 Solution.

| Component | Formula | Weight (g) |
|---|---|---|
| Sodium Hydroxide | NaNO3 | 120 |
| Water | $H_2O$ | 880 |
| Potassium Permanganate | $KMnO_4$ | 3 |
| Sodium thiocyanate | NaSCN | 3 |
| Sodium chloride | NaCl | 3 |

A quantity or batch of 750, 26 mil MH needles (needle code MH002640P manufactured by Ethicon, Inc.) was immersed in a bath containing the activating solution listed in Table 1 at 80° C. for 3 minutes, then rinsed with water, and then immersed in a bath containing the solution listed in Table 15 at 100° C. for 2 minutes. After removal from the bath, the needle surfaces were observed to remain shiny and silver. Increasing the length of the process time in the blackening bath solution did not change the color the needle. No blackened needles were obtained as the result of the treatment in the solution of this example.

Example 13

Comparative Example Inventive Process Versus Chromium (VI)-Based Process

A needle blackened by the process of the current invention as described in Example 5 was compared with a needle treated by a prior art process using chromium VI (EP1051538). The composition of the prior art process blackening bath is listed in Table 16.

TABLE 16

Formulation of Chromium VI Based Blackening Solution.

| Component | Formula | Weight (g) |
|---|---|---|
| Sulfuric acid | $H2SO4$ | 200 |
| Chromium trioxide | $CrO3$ | 200 |
| Water | $H_2O$ | 600 |

Figure 3A:
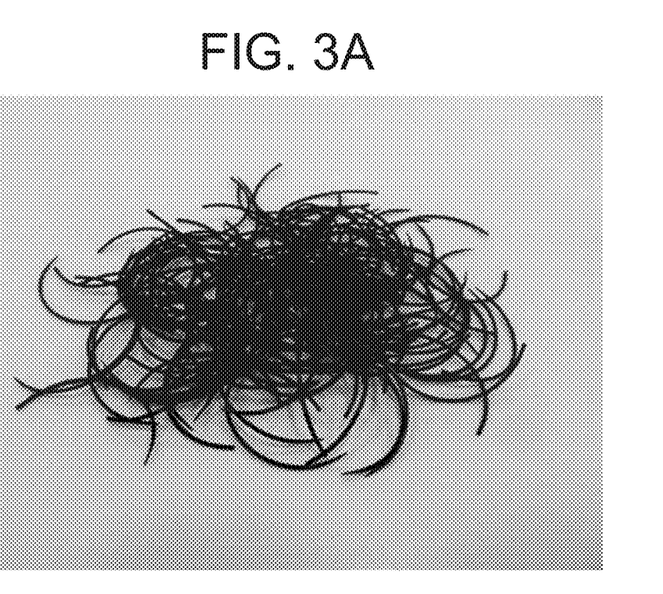
FIG. 3A is a photograph of needles blackened using the processes of the present invention (Example 6) wherein the processing time was 2 minutes to completion.
Figure 3B:
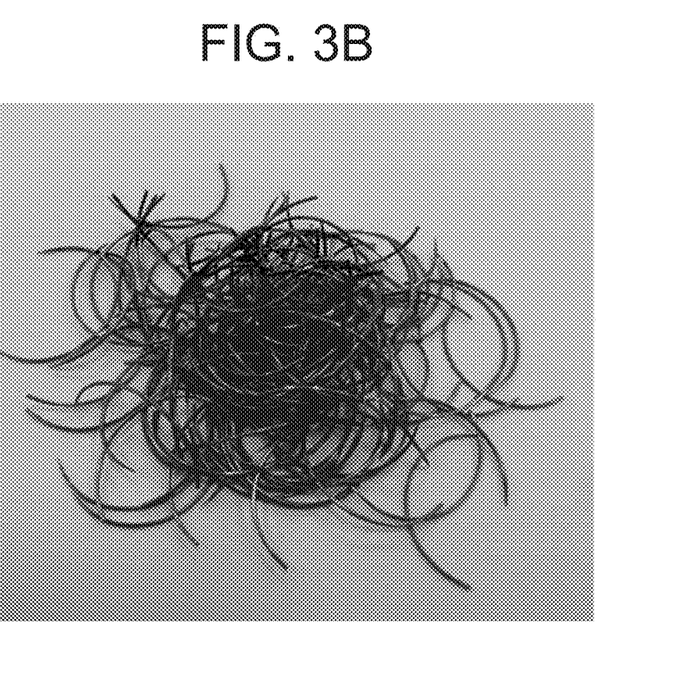
FIG. 3B is a photograph of needles identical to the needles of FIG. 3A, but treated using a blackening process of the prior art (Example 15) wherein the processing time was also 2 minutes; virtually no blackening of the surfaces of the needles can be observed.

A batch of 24 mil type 4310 MH needles similar to the needles blackened by the process of Example 5 was pretreated in a similar manner and immersed in a blackening bath solution having a composition as contained in Table 16. The needles were immersed in the coating bath of Table 16 for 2 minutes, the same treatment time for the needles of Example 6 treated with the process of the present invention. It was observed that the needles treated by the process of the present invention had all of their surfaces completely blackened. It was further observed the needles treated with the prior art process remained shiny and silver color in color, similar to the untreated 24 mil type 4310 MH needles. Photographs of the needles are seen in FIGS. 3A and 3B.

Figure 4:
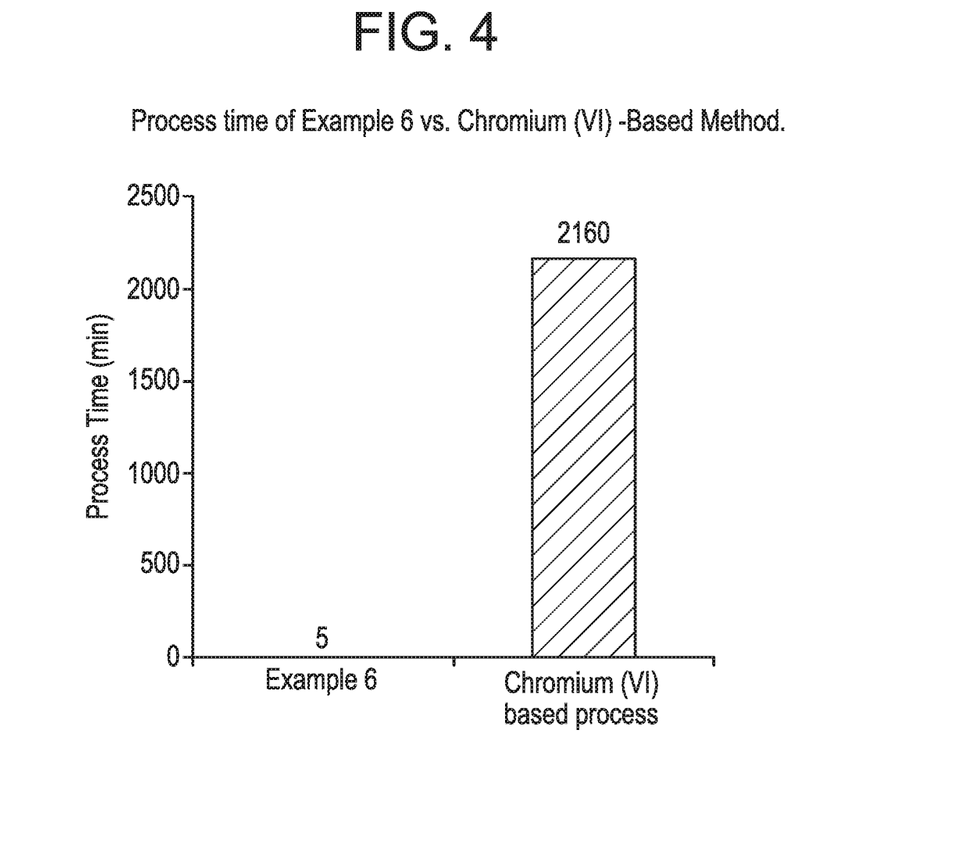
FIG. 4 is a graph showing the difference in process time between the process of the present invention described in Example 5 and a conventional Chromium (VI)-based process.

FIG. 4 is a graph showing the difference in process time between the process of the present invention described in Example 5 and a conventional Chromium (VI)-based process. It can be seen that the process time of the present invention is significantly lower and more time efficient than the Chromium (VI)-based process.

Example 14

Needles Treated in Blackening Bath without Pretreatment Bath

This example did not lead to the formation of a black oxide black layer on the surfaces of surgical needles made from Type 4310 SS alloy in comparison to the black oxide layer demonstrated and obtained in Example 1. The formulation of the blackening bath solution used in this example identical to the one used in Example 1 is listed in Table 3.

A quantity or batch of 750, 26 mil MH needles (manufactured by Ethicon, Inc.) was immersed in a bath containing the blackening solution listed in Table 3 at 100° C. for 2 minutes. The needles had not been subjected to the pretreatment step. After removal from the bath, it was observed that virtually no blackening occurred and the needle surfaces were observed to substantially remain shiny and silver. Increasing the length of the process time in the blackening bath solution to 10 minutes did not change the color of the needles. No blackened needles were obtained as a result of the treatment in the blackening solution of this example.

The novel blackening methods and blackening bath compositions of the present invention have many advantages. The advantages include significant reduction of process time, absence of toxic carcinogens, improved safety conditions, the elimination of hazardous waste, and the elimination of negative impacts on the environment.

Although this invention has been shown and described with respect to detailed embodiments thereof, it will be understood by those skilled in the art that various changes in form and detail thereof may be made without departing from the spirit and scope of the claimed invention.

We claim:
1. A method of blackening surgical needles, comprising the steps of:
   A. placing the surgical needle into a blackening bath, wherein the bath comprises:
      about 3 wt. % to about 20 wt. % of a highly soluble nitric acid salt;
      about 18 wt. % to about 38 wt. % of a strong base;
      about 50 wt. % to about 75 wt. % of water;
      about 0.2 wt. % to about 5 wt. % of a transition metal salt of a strong acid;
      about 0.2 wt. % to about 5 wt. % of a sulfur-containing reducer compound; and,

B. maintaining the needle in the blackening bath for a sufficiently effective period of time to provide a blackened coating on an outer surface of the needle.

2. The method of claim 1, wherein the transition metal salt is selected from the group consisting of nickel nitrate, cobalt nitrate, nickel sulfate, cobalt sulfate, iron nitrate, copper perchlorate, nickel perchlorate, ion perchlorate, and cobalt perchlorate.

3. The method of claim 1, wherein the sulfur-containing reducer is selected from the group consisting of, N'-diethylthiourea, sodium thiocyanate, sodium sulfide, and sodium dimethyldithiocarbamate.

4. The method of claim 1, wherein the highly soluble nitric acid salt is selected from the group consisting of sodium nitrate, potassium nitrate, and lithium nitrate.

5. The method of claim 1, wherein the strong base is selected from the group consisting of sodium hydroxide, potassium hydroxide, and lithium hydroxide.

6. A method of blackening surgical needles, comprising the steps of:
   A. placing the surgical needle into a blackening bath, wherein the bath comprises:
      about 3 wt. % to about 20 wt. % of a highly soluble nitric acid salt;
      about 18 wt. % to about 38 wt. % of a strong base;
      about 50 wt. % to about 75 wt. % of water;
      about 0.2 wt. % to about 5 wt. % of a highly soluble permanganate salt;
      about 0.2 wt. % to about 5 wt. % of a thiocyanate salt; and,
   B. maintaining the needle in the blackening bath for a sufficiently effective period of time to provide a blackened coating on an outer surface of the needle.

7. The method of claim 6, wherein the permanganate salt is selected from the group consisting of potassium permanganate, sodium permanganate, and lithium permanganate.

8. The method of claim 6, wherein the blackening bath additionally comprises a water soluble chloride salt.

9. The method of claim 6, wherein the thiocyanate salt is selected from the group consisting of sodium thiocyanate, potassium thiocyanate, and lithium thiocyanate.

10. The method of claim 6, wherein the highly soluble nitric acid salt is selected from the group consisting of sodium nitrate, potassium nitrate, and lithium nitrate.

11. The method of claim 6, wherein the strong base is selected from the group consisting of sodium hydroxide, potassium hydroxide, and lithium hydroxide.

12. The method of claim 6, wherein the blackening bath additionally comprises about 0.2 wt. % to about 5 wt. % of a molybdate salt.

13. A system for blackening stainless steel alloy surgical needles, comprising:
   a blackening bath, the blackening bath comprising:
      about 3 wt. % to about 15 wt. % of a highly soluble nitric acid salt;
      about 18 wt. % to about 38 wt. % of a strong base;
      about 50 wt. % to about 75 wt. % of water;
      about 0.2 wt. % to about 5 wt. % of a transition metal salt of a strong acid; and,
      about 0.2 wt. % to about 5 wt. % of a sulfur-containing reducer compound.

14. The system of claim 13, wherein the transition metal salt is selected from the group consisting of nickel nitrate, cobalt nitrate, nickel sulfate, cobalt sulfate, iron nitrate, copper perchlorate, nickel perchlorate, ion perchlorate, and cobalt perchlorate.

15. The system of claim 13, wherein the sulfur-containing reducer is selected from the group consisting of N'-diethylthiourea, sodium thiocyanate, sodium sulfide, and sodium dimethyldithiocarbamate.

16. The system of claim 13, wherein the highly soluble nitric acid salt is selected from the group consisting of sodium nitrate, potassium nitrate, and lithium nitrate.

17. The system of claim 13, wherein the strong base is selected from the group consisting of sodium hydroxide, potassium hydroxide, and lithium hydroxide.

18. A blackening bath, the blackening bath comprising:
   about 3 wt. % to about 20 wt. % of a highly soluble nitric acid salt;
   about 18 wt. % to about 38 wt. % of a strong base;
   about 50 wt. % to about 75 wt. % of water;
   about 0.2 wt. % to about 5 wt. % of a highly soluble permanganate salt; and,
   about 0.2 wt. % to about 5 wt. % of a thiocyanate salt.

19. The bath of claim 18, wherein the permanganate salt is selected from the group consisting of potassium permanganate, sodium permanganate, and lithium permanganate.

20. The bath of claim 18, wherein the blackening bath additionally comprises a water soluble chloride salt.

21. The bath of claim 18, wherein the thiocyanate salt is selected from the group consisting of sodium thiocyanate, potassium thiocyanate, and lithium thiocyanate.

22. The bath of claim 18, wherein the highly soluble nitric acid salt is selected from the group consisting of sodium nitrate, potassium nitrate, and lithium nitrate.

23. The bath of claim 18, wherein the strong base is selected from the group consisting of sodium hydroxide, potassium hydroxide, and lithium hydroxide.

24. The bath of claim 18, wherein the blackening bath additionally comprises about 0.2 wt. % to about 5 wt. % of a molybdate salt.

* * * * *